(12) United States Patent
    Cui et al.

(10) Patent No.: US 9,353,381 B2
(45) Date of Patent: May 31, 2016

(54) COTTON EVENT PDAB4468.19.10.3 DETECTION METHOD

(71) Applicant: Dow AgroSciences LLC, Indianapolis, IN (US)

(72) Inventors: Yunxing Cory Cui, Carmel, IN (US); Raina King, Indianapolis, IN (US); Tina Marie Kaiser, Carmel, IN (US); Andrew E. Robinson, Brownsburg, IN (US); Dayakar Pareddy, Carmel, IN (US); Sandra Grace Toledo, West Lafayette, IN (US); Leon B. Braxton, Travelers Rest, SC (US); David M. Anderson, Visalia, CA (US)

(73) Assignee: Dow AgroSciences LLC, Indianapolis, IN (US)

( * ) Notice: Subject to any disclaimer, the term of this patent is extended or adjusted under 35 U.S.C. 154(b) by 291 days.

(21) Appl. No.: 13/748,497

(22) Filed: Jan. 23, 2013

(65) Prior Publication Data

US 2013/0189681 A1    Jul. 25, 2013

Related U.S. Application Data

(60) Provisional application No. 61/589,594, filed on Jan. 23, 2012.

(51) Int. Cl.
| | |
|---|---|
| *C12Q 1/68* | (2006.01) |
| *C12P 19/34* | (2006.01) |
| *C12N 15/82* | (2006.01) |
| *C12N 9/02* | (2006.01) |

(52) U.S. Cl.
CPC .......... *C12N 15/8274* (2013.01); *C12N 9/0069* (2013.01); *C12N 9/0071* (2013.01); *C12Q 1/6876* (2013.01); *C12Q 1/6895* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2010/0281574 | A1 | 11/2010 | Zheng et al. |
| 2011/0203017 | A1 | 8/2011 | Wright et al. |

OTHER PUBLICATIONS

Kumar, et al., "Stable transformation of the cotton plastid genome and maternal inheritance of transgenes," Plant Molecular Biology, Sep. 1, 2004, pp. 203-216, vol. 56, No. 2.
International Search Report and Written Opinion for PCT/US2013/022711, dated May 14, 2013.
NCBI GenBank Accession No. AC243133.1, Nov. 13, 2010.
NCBI GenBank Accession No. AJ506369.1, Aug. 1, 2007.
NCBI GenBank Accession No. J01818.1, Dec. 19, 2006.
NCBI GenBank Accession No. AC243132.1, Nov. 13, 2010.

*Primary Examiner* — Young J Kim
(74) *Attorney, Agent, or Firm* — C. Philip Poirier; Magelby Cataxinos & Greenwood

(57) ABSTRACT

Cotton event pDAB4468.19.10.3 comprises gene expression cassettes which contain genes encoding aad-12 and pat, affording herbicide tolerance to cotton crops containing the event, and enabling methods for crop protection. Embodiments of the subject invention provide polynucleotide-related event detection methods.

5 Claims, 2 Drawing Sheets

**Plasmid Map of pDAB4468 containing the *aad12* and *pat* Expression Cassettes.**

The schematic diagram depicts the primer locations for the Taqman assay of the cotton event pDAB4468.19.10.3.

SEQUENCE LISTING

<160> NUMBER OF SEQ ID NOS: 14

<210> SEQ ID NO 1
<211> LENGTH: 1672
<212> TYPE: DNA
<213> ORGANISM: Artificial Sequence
<220> FEATURE:
<223> OTHER INFORMATION: 5' DNA flanking border sequence for cotton event pDAB4468.19.10.3

<400> SEQUENCE: 1

```
atttacccta gtcgggaagt ggtttcggga ccacaagacc gagtcgtaaa aataattact      60
tgctatattc tatgcttatt atgtgtgaac atgggtatgt ggaagtttca ctccctaatt     120
ttaccaattg catgagaaat tattaattgg gatcaatttg agacattgta aaaatatgat     180
agtctaattc aaatggtcaa ttagtgcatg taccaaaaag agtggttttg catgtcaaat     240
tgcccaaaag atgatgggtg gccggccaag gagtgataat gctccactca ttctaattta     300
aaatgtttcc ttggtgaaca aatgatggga ttaataatag aaaagggaac aaaaaaaaag     360
ggtgtcatac ttgccatcac ctagccgaaa aaccaagaaa aagaagggga taaaagaact     420
tggggggggg gattcggcca ttgcttgcct agggagagtg tttgatgttg tggcataaaa     480
aatgagggag tttgaatgct taacaaggag ggaagaagga gtgttcatat tttctttctt     540
ttgcaattgt tctaactaga ggaagaaggg gaaacaagat tcggccaagg tggtccttta     600
gaccaaggta tgtttaatgt tgtcttagag atgcatgcat gttttaaata gcccatgttc     660
aaaccttgaa tcttgttgat aacatgagca atcggtcatg agaaagtgtt ggatggagct     720
ttcggttatg gtatgtgtga gaagaacttg attctttctt acctttaagt tttgatggat     780
caagaaaaca aaaggttgtt gatgaaagaa attaatgtat taagagatta tatgaaactt     840
attcatgttt atatatgtta tatgcaacga aaatggttga tgattttgga ggtgattagc     900
ttgaatcggc cacggtatat ccataaacac gatctatgct tgttatgtta ctcatggtta     960
aaacaattcg gctatgacat tcggccatgg atggttgtat ttttttttgat gttgtttttg    1020 atgctttagg gcattgaggg ttgattatag atgaggtgag tttcttgatt taaaatttga    1080
tggatgttaa gctaattggg caaccaaagg ttcaatattt ttgttatgag gtcatatgtg    1140
catttcggcc atggtctttg cttgaatatg agatttgtaa tgtgattttc ctaaattgtc    1200
tatgaatttg gttgttgatt tcatggtaat ggtatattga atccatgaga atttagtaag    1260
gttgcattcg gcaacttact tgaaattaaa aatcgatgtc taagcttagg tgatttcgat    1320
gatgatatat gtgtatatac ataagtatat ttccagtcag catcatcaca ccaaaagtta    1380
ggcccgaata gtttgaaatt agaaagctcg caattgaggt ctacaggcca aattcgctct    1440
tagccgtaca atattactca ccggatccta accggtgtga tcatgggccg cgattaaaaa    1500
tctcaattat atttggtcta atttagtttg gtattgagta aaacaaattc gaaccaaacc    1560
aaaatataaa tatatagttt ttatatatat gcctttaaga ctttttatag aattttcttt    1620
aaaaaatatc tagaaatatt tgcgactctt ctggcatgta atatttcgtt aa            1672
```

<210> SEQ ID NO 2
<211> LENGTH: 2898
<212> TYPE: DNA
<213> ORGANISM: Artificial Sequence
<220> FEATURE:
<223> OTHER INFORMATION: 3' DNA flanking border sequence for cotton
      event pDAB4468.19.10.3

<400> SEQUENCE: 2

```
gcacatagac acacacatca tctcattgat gcttggtaat aattgtcatt agattgtttt    60
tatgcataga tgcactcgaa atcagccaat tttagacaag tatcaaacgg atgtgacttc   120
agtacattaa aaacgtccgc aatgtgttat taagttgtct aagcgtcaaa gaaaaggtta   180
tcgagtagcc gagttggaac cgtcttaccc aacacgaggt aagtcattaa gcatgtagtg   240
ggtgttattt taaatggtca taatgtgtat gtattgatgc tgattggaat gaataaatat   300
acatatatat atatgcatgt acgtatgtga tgatgaaatt gttgaatgaa tgaaaagagg   360
taagatgtac tgagttgttg atctcggcac taaacatgcg ggataaccat ttatgaccat   420
gagattggcg ctaagtgcgc gggattaaat tgtacagcac taagtgtgcg attcgactat   480
gttgcactaa gtgtgcgaaa tggatatgat gcactaagtg tgcgaattga ccatgcggca   540
ctaagtgtgc gagatggact atgtggcact aagtgtgcga tttgattacg tagcactaag   600
tgtgcgattt gattacgtag cactaagtgt gcgagttgat tatatagcac tgagtgtgcg   660
ggctcaataa atattcgtga atcattacgg acactatgtg tgcgacacta ttgagtcgat   720
cgcggacagc ggatcgggta agtgttttga gtacatggct attatgtgct atgcttatac   780
ttggtgttga gctcggtaag ttcgaaccta tgtgacaaat atacttgaag tcacgtacat   840
aaaatttatc gtaggatggg tgaaaggccg tatagtcgtt tggttgtaac gaaaataaat   900
cgatttacga aattgcttca atgtcctatt gatgagtata tagaatgtga atgcatgaat   960
tgatatgaaa ttgaattgat aagttggagg aactatggta tggttcggta tggatggagt  1020
aaattgtctc gttccatttt gtttcctctt gtgataatgt cgttgataga tggtagtgca  1080
ttgcttatga cttactgagt tataaactca ctcgatgttt ccttgtcacc cactataggt  1140
tgcttggact catctatttt tgcggggtcg ggccgtcatt gaagtcatca caccggatag  1200
caagttttgg tactttcttc ttagtgtgct tagaagatca ttttggcatg tataagctag  1260
tacgttgtgt ttgaattatg gcatgtaaac tttaagccat gcgaaaatgg cacgaatgtt  1320
cgattgagtt ggatcaaggg taggcatgaa atggacatag ttactttcgt aacagatgct  1380
ggcggcagca gtgtcatgag attgaaaaat cactaaaaat agtaggagtg gaattaattg  1440
atgaataaat tatgtaatcg aagctcgatg agtctgcttt catgaggaag taacgaaatg  1500
atcatatggg cagtatatta agagataatc agatttttgt gggacagggc cagaacggtt  1560
tctggattcc ctgctccgac tttggtaatt cattataaat taaccagaga taattagggg  1620
tcgtaccata tatgtacaga ttcctctcta agtctagttt tcatagaaac aaacggcaac  1680
agtattgaag ccccgtgcag ggagatatcc cagtcgtaat gggaaaaggt cagtgtagtc  1740
gacacctgca acttggggga ctttgactaa taaactgtaa taattggccc aaccaaaaat  1800
tctagaaaaa aatacataga tgggcaaatg agtctagttt ctgggaaaaa ttacgaaact  1860
gattttcgag ttacgaaact caagatatga ttttttaaagc ggctagtaca cagattgggc  1920
agtgtctgga aaataaattt tgtaaggggt taaagccaga taacacctcg tgttcgactc  1980
cggtgtcggt ttcgggttcg gggtgttaca ttttattggt atcagagcta tggtttagtc  2040
```

```
ggttctagga ctaccatagc acgtatgagt ctagctatac atgccataat gttaatgttt    2100
aaaagggtga tgacttctga cggttgaaat gttttttgtct tgattagtaa atggatcccg    2160
gtgaagaaag aaccctagcg gatgacgttg agagcgtagc ggctgctcct gcacaaggga    2220
cgccgcctgt tgaacctcag tcatctgcga ataatcaagg tgaggggct aaacaagcct    2280 tctttaccat gatgaatgag tgggtcgcgc agtatgcccg agccaacccg gctgtccaac    2340
aattcccaaa tttgaataat ccaccccaag agcctgtaat gccatcagtc gctgatcctg    2400
tgaggctgag taagccaccg gtagacttga ttaggaagcg tggggccgag gagttcaagg    2460
ccatagtaac tgatgatgcc gaaagggccg agttctggct tgataacacc attcgggtgc    2520
tcgatgaatt gtcatgcaca cccgatgaat gtctaaaatg tgctgtatct tgttgcgag    2580 actcagccta ctattggtgg aggaccttga tttccatagt cccgaacgag cgagtaactt    2640
gggacttctt tcaaacgaaa ttccgaaaga aatttattag ccagcggttc attgatcaga    2700
agcgtaagga gttcttggaa ctcaagcaag gccgtatgac tgtatctgaa tacgaacatg    2760
aattcgtaag acttagtagg tatgcccggg agtgtgtagc tgatgaggtt gctatgtgca    2820
aaagatttga ggaaggattg aatgaagatt taaagctact aatgggtatt ttggaaataa    2880
aggaatttgt aacactag                                                  2898
```

<210> SEQ ID NO 3
<211> LENGTH: 77
<212> TYPE: DNA
<213> ORGANISM: Artificial Sequence
<220> FEATURE:
<223> OTHER INFORMATION: 77 bp DNA fragment that is diagnostic of the 5'
      integration junction of cotton event pDAB4468.19.10.3

<400> SEQUENCE: 3

```
ggcctaactt ttggtgtgat gatgctgact ggaaatatac ttatgtatat acacatatat    60
catcatcgaa atcacct                                                   77
```

<210> SEQ ID NO 4
<211> LENGTH: 90
<212> TYPE: DNA
<213> ORGANISM: Artificial Sequence
<220> FEATURE:
<223> OTHER INFORMATION: 90 bp DNA fragment that is diagnostic of the 3'
      integration junction of cotton event pDAB4468.19.10.3

<400> SEQUENCE: 4

```
cattaaaaac gtccgcaatg tgttattaag ttgtctaagc gtcaaagaaa aggttatcga    60
gtagccgagt tggaaccgtc ttacccaaca                                     90
```

<210> SEQ ID NO 5
<211> LENGTH: 21
<212> TYPE: DNA
<213> ORGANISM: Artificial Sequence
<220> FEATURE:
<223> OTHER INFORMATION: oligonucleotide primer, ES_1910_5_F

<400> SEQUENCE: 5

```
ggcctaactt ttggtgtgat g                                              21
```

<210> SEQ ID NO 6
<211> LENGTH: 26
<212> TYPE: DNA
<213> ORGANISM: Artificial Sequence
<220> FEATURE:

<223> OTHER INFORMATION: oligonucleotide primer, ES_1910_5_R

<400> SEQUENCE: 6
aggtgatttc gatgatgata tatgtg                                          26

<210> SEQ ID NO 7
<211> LENGTH: 25
<212> TYPE: DNA
<213> ORGANISM: Artificial Sequence
<220> FEATURE:
<223> OTHER INFORMATION: oligonucleotide probe, ES_1910_5Pr

<400> SEQUENCE: 7
tgctgactgg aaatatactt atgta                                           25

<210> SEQ ID NO 8
<211> LENGTH: 22
<212> TYPE: DNA
<213> ORGANISM: Artificial Sequence
<220> FEATURE:
<223> OTHER INFORMATION: oligonucleotide primer, ES_1910_3_F

<400> SEQUENCE: 8
cattaaaaac gtccgcaatg tg                                              22

<210> SEQ ID NO 9
<211> LENGTH: 20
<212> TYPE: DNA
<213> ORGANISM: Artificial Sequence
<220> FEATURE:
<223> OTHER INFORMATION: oligonucleotide primer, ES_1910_3_R

<400> SEQUENCE: 9
tgttgggtaa gacggttcca                                                 20

<210> SEQ ID NO 10
<211> LENGTH: 16
<212> TYPE: DNA
<213> ORGANISM: Artificial Sequence
<220> FEATURE:
<223> OTHER INFORMATION: oligonucleotide probe, ES_1910_3Pr

<400> SEQUENCE: 10
aagcgtcaaa gaaaag                                                     16

<210> SEQ ID NO 11
<211> LENGTH: 28
<212> TYPE: DNA
<213> ORGANISM: Artificial Sequence
<220> FEATURE:
<223> OTHER INFORMATION: oligonucleotide primer, IC_Sah7F

<400> SEQUENCE: 11
agtttgtagg ttttgatgtt acattgag                                        28

<210> SEQ ID NO 12
<211> LENGTH: 21
<212> TYPE: DNA
<213> ORGANISM: Artificial Sequence
<220> FEATURE:
<223> OTHER INFORMATION: oligonucleotide primer, IC_Sah7R

<400> SEQUENCE: 12
gcatctttga accgcctact g                                               21

```
<210> SEQ ID NO 13
<211> LENGTH: 33
<212> TYPE: DNA
<213> ORGANISM: Artificial Sequence
<220> FEATURE:
<223> OTHER INFORMATION: oligonucleotide probe, IC_Sah7_Pr

<400> SEQUENCE: 13
aaacataaaa taatgggaac aaccatgaca tgt                                    33

<210> SEQ ID NO 14
<211> LENGTH: 6387
<212> TYPE: DNA
<213> ORGANISM: Artificial Sequence
<220> FEATURE:
<223> OTHER INFORMATION: T-strand DNA sequence of pDAB4468

<400> SEQUENCE: 14
agtcagcatc atcacaccaa aagttaggcc cgaatagttt gaaattagaa agctcgcaat        60
tgaggtctac aggccaaatt cgctcttagc cgtacaatat tactcaccgg atcctaaccg       120
gtgtgatcat gggccgcgat taaaaatctc aattatattt ggtctaattt agtttggtat       180
tgagtaaaac aaattcgaac caaaccaaaa tataaaatata tagttttat atatatgcct       240 ttaagacttt ttatagaatt ttctttaaaa aatatctaga aatatttgcg actcttctgg       300
catgtaatat ttcgttaaat atgaagtgct ccatttttat taactttaaa taattggttg       360
tacgatcact ttcttatcaa gtgttactaa aatgcgtcaa tctctttgtt cttccatatt       420
catatgtcaa aacctatcaa aattcttata tatcttttc gaatttgaag tgaaatttcg       480
ataatttaaa attaaataga acatatcatt atttaggtat catattgatt tttatactta       540
attactaaat ttggttaact ttgaaagtgt acatcaacga aaaattagtc aaacgactaa       600
aataaataaa tatcatgtgt tattaagaaa attctcctat aagaatattt taatagatca       660
tatgtttgta aaaaaaatta atttttacta cacatatat ttacttatca aaaatttgac        720
aaagtaagat taaaataata ttcatctaac aaaaaaaaaa ccagaaaatg ctgaaaaccc       780
ggcaaaaccg aaccaatcca aaccgatata gttggtttgg tttgattttg atataaaccg       840
aaccaactcg gtccatttgc acccctaatc ataatagctt taatatttca agatattatt       900
aagttaacgt tgtcaatatc ctggaaattt tgcaaaatga atcaagccta tatggctgta       960
atatgaattt aaaagcagct cgatgtggtg gtaatatgta atttacttga ttctaaaaaa      1020
atatcccaag tattaataat ttctgctagg aagaaggtta gctacgattt acagcaaagc      1080
cagaatacaa tgaaccataa agtgattgaa gctcgaaata tacgaaggaa caaatatttt      1140
taaaaaaata cgcaatgact tggaacaaaa gaaagtgata tattttttgt tcttaaacaa      1200 gcatccctc taaagaatgg cagttttcct ttgcatgtaa ctattatgct cccttcgtta       1260 caaaaattt ggactactat tgggaacttc ttctgaaaat agtggccacc gcttaattaa       1320
ggcgcgccat gcccgggcaa gcggccgcac aagtttgtac aaaaaagcag gctccgcggt      1380
gactgactga aaagcttgtc gacctgcagg tcaacggatc aggatattct tgtttaagat      1440
gttgaactct atggaggttt gtatgaactg atgatctagg accggataag ttcccttctt      1500
catagcgaac ttattcaaag aatgtttgt gtatcattct tgttacattg ttattaatga       1560
aaaaatatta ttggtcattg gactgaacac gagtgttaaa tatggaccag gccccaaata      1620
agatccattg atatatgaat taaataacaa gaataaatcg agtcaccaaa ccacttgcct      1680 ttttttaacga gacttgttca ccaacttgat acaaaagtca ttatcctatg caaatcaata     1740
```

```
atcatacaaa aatatccaat aacactaaaa aattaaaaga aatggataat ttcacaatat    1800
gttatacgat aaagaagtta cttttccaag aaattcactg atttttataag cccacttgca    1860 ttagataaat ggcaaaaaaa aacaaaaagg aaaagaaata aagcacgaag aattctagaa    1920
aatacgaaat acgcttcaat gcagtgggac ccacggttca attattgcca attttcagct    1980
ccaccgtata tttaaaaaat aaaacgataa tgctaaaaaa atataaatcg taacgatcgt    2040
taaatctcaa cggctggatc ttatgacgac cgttagaaat tgtggttgtc gacgagtcag    2100
taataaacgg cgtcaaagtg gttgcagccg gcacacacga gtcgtgttta tcaactcaaa    2160
gcacaaatac ttttcctcaa cctaaaaata aggcaattag ccaaaaacaa ctttgcgtgt    2220
aaacaacgct caatacacgt gtcattttat tattagctat tgcttcaccg ccttagcttt    2280
ctcgtgacct agtcgtcctc gtcttttctt cttcttcttc tataaaacaa tacccaaagc    2340
ttcttcttca caattcagat ttcaatttct caaaatctta aaactttct ctcaattctc    2400 tctaccgtga tcaaggtaaa tttctgtgtt cctattctc tcaaaatctt cgattttgtt    2460
ttcgttcgat cccaatttcg tatatgttct ttggtttaga ttctgttaat cttagatcga    2520
agacgatttt ctgggtttga tcgttagata tcatcttaat tctcgattag ggtttcataa    2580
atatcatccg atttgttcaa ataatttgag ttttgtcgaa taattactct tcgatttgtg    2640
atttctatct agatctggtg ttagtttcta gtttgtgcga tcgaatttgt cgattaatct    2700
gagtttttct gattaacaga gatctccatg gctcagacca ctctccaaat cacacccact    2760
ggtgccacct tgggtgccac agtcactggt gttcaccttg ccacacttga cgatgctggt    2820
ttcgctgccc tccatgcagc ctggcttcaa catgcactct tgatcttccc tgggcaacac    2880
ctcagcaatg accaacagat taccttgct aaacgctttg gagcaattga gaggattggc    2940
ggaggtgaca ttgttgccat atccaatgtc aaggcagatg gcacagtgcg ccagcactct    3000
cctgctgagt gggatgacat gatgaaggtc attgtgggca acatggcctg gcacgccgac    3060
tcaacctaca tgccagtcat ggctcaagga gctgtgttca cgcagaagt tgtcccagca    3120 gttgggggca gaacctgctt tgctgacatg agggcagcct acgatgccct tgatgaggca    3180
acccgtgctc ttgttcacca aaggtctgct cgtcactccc ttgtgtattc tcagagcaag    3240
ttgggacatg tccaacaggc cgggtcagcc tacataggtt atggcatgga caccactgca    3300
actcctctca gaccattggt caaggtgcat cctgagactg gaaggcccag cctcttgatc    3360
ggccgccatg cccatgccat ccctggcatg gatgcagctg aatcagagcg cttccttgaa    3420
ggacttgttg actgggcctg ccaggctccc agagtccatg ctcaccaatg gctgctgga    3480 gatgtggttg tgtgggacaa ccgctgtttg ctccaccgtg ctgagccctg ggatttcaag    3540
ttgccacgtg tgatgtggca ctccagactc gctggacgcc cagaaactga gggtgctgcc    3600
ttggtttgag tagttagctt aatcacctag agctcggtca ccagcataat ttttattaat    3660
gtactaaatt actgttttgt taaatgcaat tttgctttct cgggatttta atatcaaat    3720 ctatttagaa atacacaata ttttgttgca ggcttgctgg agaatcgatc tgctatcata    3780
aaaattacaa aaaaattta tttgcctcaa ttatttttagg attggtatta aggacgctta    3840
aattatttgt cgggtcacta cgcatcattg tgattgagaa gatcagcgat acgaaatatt    3900
cgtagtacta tcgataattt atttgaaaat tcataagaaa agcaaacgtt acatgaattg    3960
atgaaacaat acaagacag ataaagccac gcacatttag gatattggcc gagattactg    4020
aatattgagt aagatcacgg aatttctgac aggagcatgt cttcaattca gcccaaatgg    4080
cagttgaaat actcaaaccg ccccatatgc aggagcggat cattcattgt ttgtttggtt    4140
```

```
gcctttgcca acatgggagt ccaaggttgc ggccgcgcgc cgacccagct ttcttgtaca    4200
aagtggttgc ggccgcttaa ttaaatttaa atgcccgggg gtttaaacgc ggccgcttaa    4260
ttaaggccgg cctgcagcaa acccagaagg taattatcca agatgtagca tcaagaatcc    4320
aatgtttacg ggaaaaacta tggaagtatt atgtaagctc agcaagaagc agatcaatat    4380
gcggcacata tgcaacctat gttcaaaaat gaagaatgta cagatacaag atcctatact    4440
gccagaatac gaagaagaat acgtagaaat tgaaaagaa gaaccaggcg aagaaaagaa    4500
tcttgaagac gtaagcactg acgacaacaa tgaaagaag aagataaggt cggtgattgt    4560
gaaagagaca tagaggacac atgtaaggtg gaaaatgtaa gggcggaaag taaccttatc    4620
acaaaggaat cttatccccc actacttatc cttttatatt tttccgtgtc attttttgccc    4680 ttgagtttc ctatataagg aaccaagttc ggcattgtg aaaacaagaa aaatttggt    4740 gtaagctatt ttctttgaag tactgaggat acaacttcag agaaatttgt aagtttgtag    4800
atctccatgt ctccggagag gagaccagtt gagattaggc cagctacagc agctgatatg    4860
gccgcggttt gtgatatcgt taaccattac attgagacgt ctacagtgaa ctttaggaca    4920
gagccacaaa caccacaaga gtggattgat gatctagaga ggttgcaaga tagataccct    4980
tggttggttg ctgaggttga gggtgttgtg gctggtattg cttacgctgg gccctggaag    5040
gctaggaacg cttacgattg gacagttgag agtactgttt acgtgtcaca taggcatcaa    5100
aggttgggcc taggatccac attgtacaca catttgctta agtctatgga ggcgcaaggt    5160
tttaagtctg tggttgctgt tataggcctt ccaaacgatc catctgttag gttgcatgag    5220
gctttgggat acacagcccg gggtacattg cgcgcagctg gatacaagca tggtggatgg    5280
catgatgttg gttttggca aagggattt gagttgccag ctcctccaag gccagttagg    5340
ccagttaccc agatctgagg taccctgagc ttgagcttat gagcttatga gcttagagct    5400
cggatccact agtaacggcc gccagtgtgc tggaattcgc ccttgactag ataggcgccc    5460
agatcggcgg caatagcttc ttagcgccat cccgggttga tcctatctgt gttgaaatag    5520
ttgcggtggg caaggctctc tttcagaaag acaggcggcc aaaggaaccc aaggtgaggt    5580
gggctatggc tctcagttcc ttgtggaagc gcttggtcta aggtgcagag gtgttagcgg    5640
gatgaagcaa aagtgtccga ttgtaacaag atatgttgat cctacgtaag gatattaaag    5700
tatgtattca tcactaatat aatcagtgta ttccaatatg tactacgatt tccaatgtct    5760
ttattgtcgc cgtatgtaat cggcgtcaca aaataatccc cggtgacttt cttttaatcc    5820
aggatgaaat aatatgttat tataatttt gcgatttggt ccgttatagg aattgaagtg    5880
tgcttgcggt cgccaccact cccatttcat aattttacat gtatttgaaa ataaaaatt    5940 tatggtattc aatttaaaca cgtatacttg taaagaatga tatcttgaaa gaaatatagt    6000
ttaaatattt attgataaaa taacaagtca ggtattatag tccaagcaaa aacataaatt    6060
tattgatgca agtttaaatt cagaaatatt tcaataactg attatatcag ctggtacatt    6120
gccgtagatg aaagactgag tgcgatatta tggtgtaata catagcggcc gggtttctag    6180
tcaccggtta ggatccgttt aaactcgagg ctagcgcatg cacatagaca cacacatcat    6240
ctcattgatg cttggtaata attgtcatta gattgttttt atgcatagat gcactcgaaa    6300
tcagccaatt ttagacaagt atcaaacgga tgtgacttca gtacattaaa aacgtccgca    6360
atgtgttatt aagttgtcta agcgtca                                       6387
```

COTTON EVENT PDAB4468.19.10.3 DETECTION METHOD

CROSS-REFERENCE TO RELATED APPLICATION

This application claims the benefit of U.S. Provisional Patent Application Ser. No. 61/589,594, filed Feb. 23, 2012, the disclosure of which is hereby incorporated herein in its entirety by this reference.

BACKGROUND OF THE INVENTION

The gene encoding AAD-12 (aryloxyalkanoate dioxygenase-12) is capable of imparting commercial levels of tolerance to the phenoxyacetic acid herbicides, 2,4-D and MCPA, and the pyridyloxyacetic acid herbicides, triclopyr and fluroxypyr, when expressed in transgenic plants. The gene encoding PAT (phosphinothricin acetyltransferase) is capable of imparting tolerance to the herbicide phoshpinothricin (glufosinate) when expressed in transgenic plants. PAT has been successfully expressed in cotton for use both as a selectable marker, and to impart commercial levels of tolerance to the herbicide glufosinate in transgenic plants.

The expression of transgenes in plants is known to be influenced by their location in the plant genome, perhaps due to chromatin structure (e.g., heterochromatin) or the proximity of transcriptional regulatory elements (e.g., enhancers) close to the integration site (Weising et al., Ann. Rev. Genet 22:421-477, 1988). The presence of the transgene at different locations in the genome will influence the overall phenotype of the plant in different ways. For example, it has been observed in plants and in other organisms that there may be a wide variation in levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different events and screen those events for a single event that has desired transgene expression levels and patterns for commercial purposes. As such, it is often necessary to screen a large number of events in order to identify an event characterized by optimal expression of an introduced gene of interest. An event that has desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

It is desirable to be able to detect the presence of a particular event in order to determine whether progeny of a sexual cross contain a transgene or group of transgenes of interest. In addition, a method for detecting a particular event would be helpful for complying with regulations requiring the pre-market approval and labeling of food and fiber derived from recombinant crop plants, for example, or for use in environmental monitoring, monitoring traits in crops in the field, or monitoring products derived from a crop harvest, as well as for use in ensuring compliance of parties subject to regulatory or contractual terms.

It is possible to detect the presence of a transgenic event by any nucleic acid detection method known in the art including, but not limited to, the polymerase chain reaction (PCR) or DNA hybridization using nucleic acid probes. These detection methods generally focus on frequently used genetic elements, such as promoters, terminators, marker genes, etc., because for many DNA constructs, the coding region is interchangeable. As a result, such methods may not be useful for discriminating between different events, particularly those produced using the same DNA construct or very similar constructs unless the DNA sequence of the flanking DNA adjacent to the inserted heterologous DNA is known. For example, an event-specific PCR assay is described in United States Patent Application 2006/0070139 for maize event DAS-59122-7. It would be desirable to have a simple and discriminative method for the identification of cotton event pDAB4468.19.10.3.

BRIEF SUMMARY OF THE INVENTION

Embodiments of the present invention relate to a method for detecting a new insect resistant and herbicide tolerant transgenic cotton transformation event, designated as cotton event pDAB4468.19.10.3, comprising aad-12 and pat as described herein, inserted into a specific site within the genome of a cotton cell. Representative cotton seed has been deposited with the American Type Culture Collection (ATCC), 10801 University Boulevard, Manassas, Va., 20110. The deposit, designated as ATCC Deposit No. PTA-12457, was made on behalf of Dow AgroSciences LLC on Jan. 23, 2012. This deposit was made and will be maintained in accordance with and under the terms of the Budapest Treaty with respect to seed deposits for the purposes of patent procedure.

The DNA of cotton plants containing this event includes the junction/flanking sequences described herein that characterize the location of the inserted DNA within the cotton genome. SEQ ID NO:1 and SEQ ID NO:2 are diagnostic for cotton event pDAB4468.19.10.3. More particularly, sequences surrounding the junctions at by 1354/1355 of SEQ ID NO:1, and by 168/169 of SEQ ID NO:2 are diagnostic for cotton event pDAB4468.19.10.3. Paragraphs [0012] and [0013] below describe examples of sequences comprising these junctions that are characteristic of DNA of cotton plants containing cotton event pDAB4468.19.10.3.

In another embodiment, the invention provides a method of detecting cotton event pDAB4468.19.10.3 in a sample comprising cotton DNA, said method comprising:
  (a) contacting said sample with a first primer at least 10 bp in length that selectively binds to a flanking sequence within by 1-1354 of SEQ ID NO:1 or the complement thereof, and a second primer at least 10 bp in length that selectively binds to an insert sequence within by 1355-1672 of SEQ ID NO:1 or the complement thereof; and
  (b) assaying for an amplicon generated between said primers; or,
  (c) contacting said sample with a first primer at least 10 bp in length that selectively binds to an insert sequence within by 1-168 of SEQ ID NO:2 or the complement thereof, and a second primer at least 10 bp in length that selectively binds to a flanking sequence within by 169-2898 of SEQ ID NO:2 or the complement thereof; and
  (d) assaying for an amplicon generated between said primers.

In another embodiment, the invention provides a method of detecting cotton event pDAB4468.19.10.3 comprising:
  (a) contacting said sample with a first primer that selectively binds to a flanking sequence selected from the group consisting of by 1-1354 of SEQ ID NO:1 and by 169-2898 of SEQ ID NO:2, and complements thereof;

and a second primer that selectively binds to SEQ ID NO:14, or the complement thereof;

(b) subjecting said sample to polymerase chain reaction; and (c) assaying for an amplicon generated between said primers.

In another embodiment, the invention provides an isolated DNA molecule that is diagnostic for cotton event pDAB4468.19.10.3. Such molecules include, in addition to SEQ ID NOS: 1 and 2, molecules of at least 50 bp in length which comprise a polynucleotide sequence which spans the by 1354/1355 junction of SEQ ID NO:1, and molecules of at least 50 bp in length which comprise a polynucleotide sequence which spans the by 168/169 junction of SEQ ID NO:2. Examples are by 1329-1380 of SEQ ID NO:1; by 1304-1405 of SEQ ID NO:1; by 1254-1455 of SEQ ID NO:1; by 1154-1555 of SEQ ID NO:1; by 1054-1655 of SEQ ID NO:1; by 143-194 of SEQ ID NO:2; by 118-219 of SEQ ID NO:2; by 68-269 of SEQ ID NO:2; and by 1-369 of SEQ ID NO:2, and complements thereof.

Additionally, embodiments of the invention provide assays for detecting the presence of the subject event in a sample (of cotton, for example). The assays can be based on the DNA sequence of the recombinant construct, inserted into the cotton genome, and on the genomic sequences flanking the insertion site. Kits and conditions useful in conducting the assays are also provided.

Embodiments of the invention relate in part to the cloning and analysis of the DNA sequences of the border regions resulting from insertion of T-DNA from pDAB4468 in transgenic cotton lines. These sequences are unique. Based on the insert and junction sequences, event-specific primers can be and were generated. PCR analysis demonstrated that these events can be identified by analysis of the PCR amplicons generated with these event-specific primer sets. Thus, these and other related procedures can be used to uniquely identify cotton lines comprising the event of the subject disclosure.

BRIEF DESCRIPTION OF THE SEQUENCES

SEQ ID NO:1 is the 5' DNA flanking border sequence for cotton event pDAB4468.19.10.3. Nucleotides 1-1354 are genomic sequence. Nucleotides 1355-1672 are insert sequence.

SEQ ID NO:2 is the 3' DNA flanking border sequence for cotton event pDAB4468.19.10.3. Nucleotides 1-168 are insert sequence. Nucleotides 169-2898 are genomic sequence.

SEQ ID NO:3 is a 77 bp DNA fragment that is diagnostic of the 5' integration junction of cotton event pDAB4468.19.10.3.

SEQ ID NO:4 is a 90 bp DNA fragment that is diagnostic of the 3' integration junction of cotton event pDAB4468.19.10.3.

SEQ ID NO:5 is oligonucleotide primer, ES_1910_5_F, which was used for the TaqMan® assay to detect the 5' border of cotton event 9582.814.19.1.

SEQ ID NO:6 is oligonucleotide primer, ES_1910_5_R, which was used for the TaqMan® assay to detect the 5' border of cotton event 9582.814.19.1.

SEQ ID NO:7 is oligonucleotide probe, ES_1910_5Pr, which was used for the TaqMan® assay to detect the 5' border of cotton event 9582.814.19.1. This probe had a VIC fluorescent moiety added to the 5' end and an MGB quencher added to the 3' end.

SEQ ID NO:8 is oligonucleotide primer, ES_1910_3_F, which was used for the TaqMan® assay to detect the 3' border of cotton event 9582.814.19.1.

SEQ ID NO:9 is oligonucleotide primer, ES_1910_3_R, which was used for the TaqMan® assay to detect the 3' border of cotton event 9582.814.19.1.

SEQ ID NO:10 is oligonucleotide probe, ES_1910_3Pr, which was used for the TaqMan® assay to detect the 5' border of cotton event 9582.814.19.1. This probe had a VIC fluorescent moiety added to the 5' end and an MGB quencher added to the 3' end.

SEQ ID NO:11 is oligonucleotide primer, IC_Sah7F, which was used for the TaqMan® assay to detect the endogenous reference gene, Sah7 (GenBank: AY117065.1).

SEQ ID NO:12 is oligonucleotide primer, IC_Sah7R, which was used for the TaqMan® assay to detect the endogenous reference gene, Sah7 (GenBank: AY117065.1).

SEQ ID NO:13 is oligonucleotide probe, IC_Sah7_Pr, which was used for the TaqMan® assay to detect the endogenous reference gene, Sah7 (GenBank: AY117065.1). This probe had a Cy5fluorescent moiety added to the 5' end and a BHQ2 quencher added to the 3' end.

SEQ ID NO:14 is the T-strand DNA sequence of pDAB4468.

DETAILED DESCRIPTION OF THE INVENTION

Figure 1:
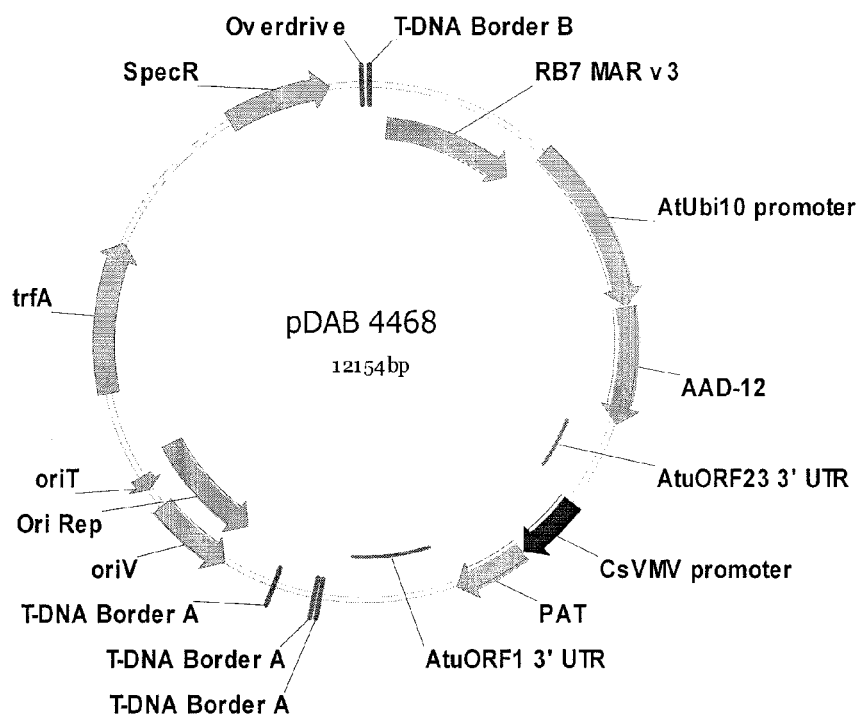
FIG. 1 is a plasmid map of pDAB4468 containing the aad-12 and pat expression cassette.

Both ends of cotton event pDAB4468.19.10.3 insertion have been sequenced and characterized. Event specific assays were developed. The event has also been mapped onto the cotton genome (chromosome 3 of the A sub-genome). The event can be introgressed into further elite lines.

As alluded to above in the Background section, the introduction and integration of a transgene into a plant genome involves some random events (hence the name "event" for a given insertion that is expressed). That is, with many transformation techniques such as *Agrobacterium* transformation, the biolistic transformation (i.e., gene gun), and silicon carbide mediated transformation (i.e., WHISKERS), it is unpredictable where in the genome a transgene will become inserted. Thus, identifying the flanking plant genomic DNA on both sides of the insert can be important for identifying a plant that has a given insertion event. For example, PCR primers can be designed that generate a PCR amplicon across the junction region of the insert and the host genome. This PCR amplicon can be used to identify a unique or distinct type of insertion event.

Definitions and examples are provided herein to help describe the embodiments of the present invention and to guide those of ordinary skill in the art to practice those embodiments. Unless otherwise noted, terms are to be understood according to conventional usage by those of ordinary skill in the relevant art. The nomenclature for DNA bases as set forth at 37 CFR §1.822 is used.

As used herein, the term "progeny" denotes the offspring of any generation of a parent plant which comprises cotton event pDAB4468.19.10.3.

A transgenic "event" is produced by transformation of plant cells with heterologous DNA, i.e., a nucleic acid construct that includes the transgenes of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA, which would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" or "border sequence" spans the point at which DNA inserted into the genome is linked to DNA from the cotton native genome flanking the insertion point, the identification or detection of one or the other junction sequences in a plant's genetic material being sufficient to be diagnostic for the event. Included are the DNA sequences that span the insertions in herein-described cotton events and similar lengths of flanking DNA. Specific examples of such diagnostic sequences are provided herein; however, other sequences that overlap the junctions of the insertions, or the junctions of the insertions and the genomic sequence, are also diagnostic and could be used in accordance with embodiments of the invention of the subject disclosure.

Embodiments of the invention relate in part to event identification using such flanking, junction, and insert sequences. Related PCR primers and amplicons are included in embodiments of the invention. In accordance with embodiments of the subject invention, PCR analysis methods using amplicons that span across inserted DNA and its borders can be used to detect or identify commercialized transgenic cotton varieties or lines derived from the subject proprietary transgenic cotton lines.

The flanking/junction sequences are diagnostic for cotton event pDAB4468.19.10.3. Based on these sequences, event-specific primers were generated. PCR analysis demonstrated that these cotton lines can be identified in different cotton genotypes by analysis of the PCR amplicons generated with these event-specific primer sets. Thus, these and other related procedures can be used to uniquely identify these cotton lines. The sequences identified herein are unique.

Detection techniques of embodiments of the subject invention are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit cotton breeding programs as well as quality control, especially for commercialized transgenic cotton seeds. PCR detection kits for these transgenic cotton lines can also now be made and used. This is also beneficial for product registration and product stewardship.

Furthermore, flanking cotton/genomic sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of all the subject disclosure, it should be clear that embodiments of the subject invention include seeds available under the ATCC Deposit No. identified in paragraph [0005]. Embodiments of the invention also include a herbicide-tolerant cotton plant grown from a seed deposited with the ATCC Deposit No. identified in paragraph [0005]. Embodiments of the invention also include parts of said plant, such as leaves, tissue samples, seeds produced by said plant, pollen, and the like (wherein these parts of the plant comprise aad-12, and pat, and SEQ ID NOS: 1 and 2).

As used herein, the term "cotton" means *Gossypium hirsutum* and includes all varieties thereof that can be bred with a cotton plant.

The DNA molecules of embodiments of the invention can be used as molecular markers in a marker assisted breeding (MAB) method. DNA molecules of embodiments of the invention can be used in methods (such as, AFLP markers, RFLP markers, RAPD markers, SNPs, and SSRs) that identify genetically linked agronomically useful traits, as is known in the art. The herbicide-tolerance traits can be tracked in the progeny of a cross with a cotton plant of embodiments of the subject invention (or progeny thereof and any other cotton cultivar or variety) using the MAB methods. The DNA molecules are markers for this trait, and MAB methods that are well known in the art can be used to track the hebicide-tolerant trait(s) in cotton plants where at least one cotton line of embodiments of the subject invention, or progeny thereof, was a parent or ancestor. The methods of embodiments of the invention can be used to identify any cotton variety having the subject event.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations.

"Commercial Utility" is defined as having good plant vigor and high fertility, such that the crop can be produced by farmers using conventional farming equipment, and the oil with the described components can be extracted from the seed using conventional crushing and extraction equipment.

"Agronomically elite" means that a line has desirable agronomic characteristics such as yield, maturity, disease resistance, and the like, in addition to the herbicide tolerance due to the subject event(s). Any and all of these agronomic characteristics and data points can be used to identify such plants, either as a point or at either end or both ends of a range of characteristics used to define such plants.

As one skilled in the art will recognize in light of this disclosure, preferred embodiments of detection kits, for example, can include probes and/or primers directed to and/or comprising "junction sequences" or "transition sequences" (where the cotton genomic flanking sequence meets the insert sequence). For example, this includes a polynucleotide probes, primers, and/or amplicons designed to identify one or both junction sequences (where the insert meets the flanking sequence). One common design is to have one primer that hybridizes in the flanking region, and one primer that hybridizes in the insert. Such primers are often each about at least ~15 residues in length. With this arrangement, the primers can be used to generate/amplify a detectable amplicon that indicates the presence of an event of an embodiment of the subject invention. These primers can be used to generate an amplicon that spans (and includes) a junction sequence as indicated above.

The primer(s) "touching down" in the flanking sequence is typically not designed to hybridize beyond about 1200 bases or so beyond the junction. Thus, typical flanking primers would be designed to comprise at least 15 residues of either strand within 1200 bases into the flanking sequences from the beginning of the insert. That is, primers comprising a sequence of an appropriate size from (or hybridizing to) base pairs 154-1672 of SEQ ID NO:1 and/or base pairs 1-1369 of SEQ ID NO:2 are within the scope of embodiments of the subject invention. Insert primers can likewise be designed anywhere on the insert, but base pairs 1-6387 of SEQ ID NO:14, can be used, for example, non-exclusively for such primer design.

One skilled in the art will also recognize that primers and probes can be designed to hybridize, under a range of standard hybridization and/or PCR conditions wherein the primer or probe is not perfectly complementary to the exemplified sequence. That is, some degree of mismatch or degeneracy can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of an embodiment of the subject invention.

It should be noted that errors in PCR amplification can occur which might result in minor sequencing errors, for example. That is, unless otherwise indicated, the sequences listed herein were determined by generating long amplicons from cotton genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of embodiments of the subject invention.

It should also be noted that it is not uncommon for some genomic sequence to be deleted, for example, when a sequence is inserted during the creation of an event. Thus, some differences can also appear between the subject flanking sequences and genomic sequences listed in GENBANK, for example.

Components of the DNA sequence "insert" are illustrated in the Figures and are discussed in more detail below in the Examples. The DNA polynucleotide sequences of these components, or fragments thereof, can be used as DNA primers or probes in the methods of embodiments of the invention.

In some embodiments of the invention, compositions and methods are provided for detecting the presence of the transgene/genomic insertion region, in plants and seeds and the like, from a cotton plant. DNA sequences are provided that comprise the subject 5' transgene/genomic insertion region junction sequence provided herein (between base pairs 1354/1355 of SEQ ID NO:1), segments thereof, and complements of the exemplified sequences and any segments thereof. DNA sequences are provided that comprise the subject 3' transgene/genomic insertion region junction sequence provided herein (between base pairs 168/169 of SEQ ID NO:2), segments thereof, and complements of the exemplified sequences and any segments thereof. The insertion region junction sequence spans the junction between heterologous DNA inserted into the genome and the DNA from the cotton cell flanking the insertion site. Such sequences can be diagnostic for the given event.

Based on these insert and border sequences, event-specific primers can be generated. PCR analysis demonstrated that cotton lines of embodiments of the subject invention can be identified in different cotton genotypes by analysis of the PCR amplicons generated with these event-specific primer sets. These and other related procedures can be used to uniquely identify these cotton lines. Thus, PCR amplicons derived from such primer pairs are unique and can be used to identify these cotton lines.

In some embodiments, DNA sequences that comprise a contiguous fragment of the novel transgene/genomic insertion region are an aspect of embodiments of this invention. Included are DNA sequences that comprise a sufficient length of polynucleotides of transgene insert sequence and a sufficient length of polynucleotides of cotton genomic sequence from one or more of the three aforementioned cotton plants and/or sequences that are useful as primer sequences for the production of an amplicon product diagnostic for one or more of these cotton plants.

Related embodiments pertain to DNA sequences that comprise at least 10, 11, 12, 13, 14, 15, 16, 17, 18, 19, 20, 21, 22, 23, 24, 25, or more contiguous nucleotides of a transgene portion of a DNA sequence identified herein (such as SEQ ID NO:1 and segments thereof), or complements thereof, and a similar length of flanking cotton DNA sequence from these sequences, or complements thereof. Such sequences are useful as DNA primers in DNA amplification methods. The amplicons produced using these primers are diagnostic for any of the cotton events referred to herein. Therefore, embodiments of the invention also include the amplicons produced by such DNA primers.

Embodiments of this invention also include methods of detecting the presence of DNA, in a sample, that corresponds to the cotton event referred to herein. Such methods can comprise: (a) contacting the sample comprising DNA with a primer set that, when used in a nucleic acid amplification reaction with DNA from at least one of these cotton events, produces an amplicon that is diagnostic for said event(s); (b) performing a nucleic acid amplification reaction, thereby producing the amplicon; and (c) detecting the amplicon.

Further detection methods of embodiments of the subject invention include a method of detecting the presence of a DNA, in a sample, corresponding to said event, wherein said method comprises: (a) contacting the sample comprising DNA with a probe that hybridizes under stringent hybridization conditions with DNA from said cotton event and which does not hybridize under the stringent hybridization conditions with a control cotton plant (non-event-of-interest DNA); (b) subjecting the sample and probe to stringent hybridization conditions; and (c) detecting hybridization of the probe to the DNA.

DNA detection kits can be developed using the compositions disclosed herein and methods well known in the art of DNA detection. The kits are useful for identification of the subject cotton event DNA in a sample and can be applied to methods for breeding cotton plants containing this DNA. The kits contain DNA sequences complementary to the amplicons, for example, disclosed herein, or to DNA sequences complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe can hybridize to a strand of a target nucleic acid, in the case of the embodiments of the invention, to a strand of genomic DNA from one of said cotton events, whether from a cotton plant or from a sample that includes DNA from the event. Probes in accordance with embodiments of the invention include not only deoxyribonucleic or ribonucleic acids but also polyamides and other probe materials that bind specifically to a target DNA sequence and can be used to detect the presence of that target DNA sequence.

"Primers" are isolated/synthesized nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of embodiments of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, or 1000, or 2000, or 5000 polynucleotides or more in length. Such probes and primers hybridize specifically to a target sequence under stringent hybridization conditions. Preferably, probes and primers in accordance with embodiments of the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of embodiments of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Molecules that exhibit complete complementarity will generally hybridize to one another with sufficient stability to permit them to remain annealed to one another under conventional "high-stringency" conditions. Conventional high-stringency conditions are described by Sambrook et al., 1989.

Two molecules are said to exhibit "minimal complementarity" if they can hybridize to one another with sufficient stability to permit them to remain annealed to one another under at least conventional "low-stringency" conditions. Conventional low-stringency conditions are described by Sambrook et al., 1989. In order for a nucleic acid molecule to serve as a primer or probe it need only exhibit minimal complementary in sequence to be able to form a stable double-stranded structure under the particular solvent and salt concentrations employed.

The term "stringent condition" or "stringency conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58.

Depending on the application envisioned, one can use varying conditions of stringent conditions or polynucleotide sequence degeneracy of a probe or primer to achieve varying degrees of selectivity of hybridization towards the target sequence. For applications requiring high selectivity, one will typically employ relatively stringent conditions for hybridization of one polynucleotide sequence with a second polynuclotide sequence, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well known to those of skill in the art, and the teachings of U.S. Pat. Nos. 4,965,188 and 5,176,995 are exemplary of the methods of hybridization analyses.

A nucleic acid of an embodiment of the present invention will specifically hybridize to one or more of the primers (or amplicons or other sequences) exemplified or suggested herein, including complements and fragments thereof, under high stringency conditions. In one aspect of the present invention, a marker nucleic acid molecule of an embodiment of the present invention has the nucleic acid sequence as set forth herein in one of the exemplified sequences, or complements and/or fragments thereof.

In another aspect of the present invention, a marker nucleic acid molecule of an embodiment of the present invention shares between 80% and 100% or 90% and 100% sequence identity with such nucleic acid sequences. In a further aspect of an embodiment of the present invention, a marker nucleic acid molecule of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the cotton plant resulting from a sexual cross contains transgenic event genomic DNA from the cotton plant of an embodiment of the present invention, DNA extracted from a cotton plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. No. 4,683,195 and U.S. Pat. No. 4,683,202. PCR amplification methods have been developed to amplify up to 22 kb of genomic DNA. These methods as well as other methods known in the art of DNA amplification may be used in the practice of embodiments of the present invention. The sequence of the heterologous transgene DNA insert or flanking genomic sequence from a subject cotton event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where a DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled ddNTPs specific for the expected next base. Analysis of a bound product can be completed via quantitating the amount of fluorescent signal. A fluorescent signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is designed to hybridize to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of an embodiment of the present invention. Following this method, an oligonucleotide is designed which overlaps the genomic flanking and inserted DNA junction. The oligonucleotide is hybridized to the single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation of the fluorescently labeled ddNTP can be measured as a change in polarization using a fluorometer. A change in polarization indicates the presence of the transgene insert/flanking sequence due to successful amplification, hybridization, and single base extension.

TaqMan® (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, the Taq DNA polymerase proofreading mechanism releases the fluorescent moiety away from the quenching moiety on the FRET probe. A fluorescent signal indicates the presence of the flanking/transgene insert sequence due to successful amplification and hybridization.

Molecular Beacons have been described for use in polynucleotide sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed a location in the cotton genome that is excellent for an insertion, embodiments of the subject invention also comprise a cotton seed and/or a cotton plant comprising at least one non-cotton event pDAB4468.19.10.3 insert in the general vicinity of this genomic location. One option is to substitute a different insert in place of the one from cotton event pDAB4468.19.10.3 exemplified herein. In general, targeted homologous recombination, for example, is employed in particular embodiments. This type of technology is the subject of, for example, WO 03/080809 A2 and the corresponding published U.S. application (US 20030232410). Thus, embodiments of the subject invention include plants and plant cells comprising a heterologous insert (in place of or with multi-copies of the aad-12 or pat genes), flanked by all or a recognizable part of the flanking sequences identified herein (bp 1-1354 of SEQ ID NO:1 and by 169-2898 of SEQ ID NO:2). An additional copy (or additional copies) of an aad-12 or pat gene could also be targeted for insertion in this/these manner(s).

All patents, patent applications, provisional applications, and publications referred to or cited herein are incorporated by reference in their entirety to the extent they are not inconsistent with the explicit teachings of this specification.

The following examples are included to illustrate procedures for practicing embodiments of the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention. Unless otherwise indicated, all percentages are by weight and all solvent mixture proportions are by volume unless otherwise noted.

The following abbreviations are used unless otherwise indicated.

bp base pair
° C. degrees Celsius
DNA deoxyribonucleic acid
EDTA ethylenediaminetetraacetic acid kb kilobase
μg microgram
μL microliter
mL milliliter
M molar mass
PCR polymerase chain reaction
PTU plant transcription unit or expression cassette
SDS sodium dodecyl sulfate
SSC a buffer solution containing a mixture of sodium chloride and sodium citrate, pH 7.0
TBE a buffer solution containing a mixture of Tris base, boric acid and EDTA, pH 8.3

EXAMPLES

Example 1

Event Specific TaqMan® Assay

Figure 2:
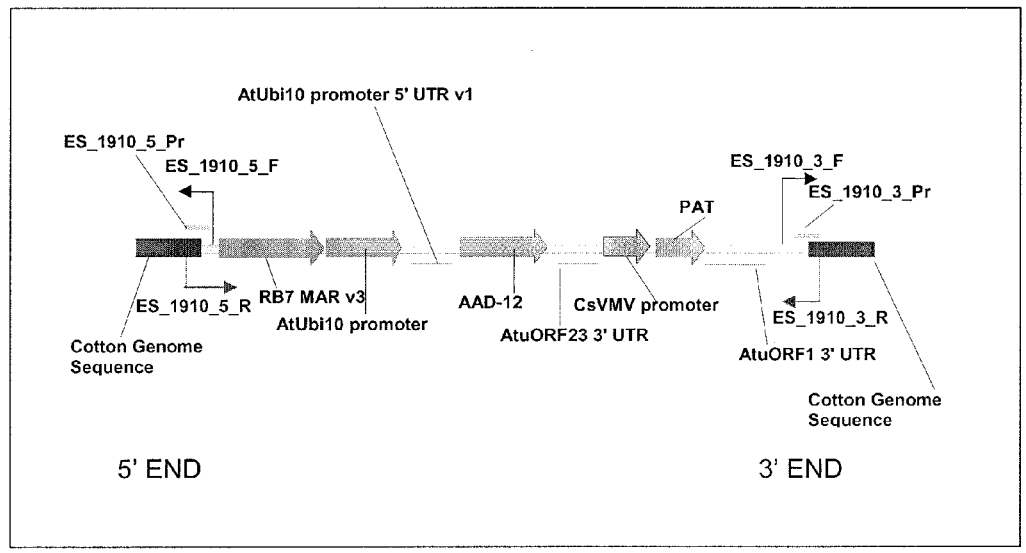
FIG. 2 depicts the primer and probe locations for the TaqMan® assay of the cotton event pDAB4468.19.10.3.

Event specific TaqMan® assays were developed to detect the presence of cotton event pDAB4468.19.10.3 plants in breeding populations. Cotton event pDAB4468.19.10.3 contains the T-strand of the binary vector pDAB4468 (FIG. 1). For specific detection of cotton event pDAB4468.19.10.3, two sets of TaqMan® primers and probes were designed according to the DNA sequences located in the 5' (SEQ ID NO:1) or 3' (SEQ ID NO:2) insert-to-plant junction (FIG. 2). One of the event specific assays for cotton event pDAB4468.19.10.3 was designed to specifically detect a 77 bp DNA fragment (SEQ ID NO:3) that spans the 5' integration junction using two primers and a target-specific MGB probe synthesized by Applied Biosystems (ABI) containing the VIC reporter at its 5'end. A second event specific assay for cotton event pDAB4468.19.10.3 was designed to specifically target an 90 bp DNA fragment (SEQ ID NO:4) that spans the 3' integration junction using two specific primers and a target-specific MGB probe synthesized by ABI containing the VIC reporter at its 5'end. Specificity of this TaqMan® detection method for cotton event pDAB4468.19.10.3 was tested against other AAD12 and PAT cotton events and the non-transgenic cotton variety (Coker310). All assays were run in duplex format with a TaqMan® assay designed to detect the known single-copy cotton specific endogenous reference gene, Sah7 (GenBank: AY117065.1).

Example 1.1 gDNA Isolation

Genomic DNA was extracted using modified Qiagen Dneasy 96 plant DNA Kit™ (Qiagen, Valencia, Calif.). Fresh cotton leaf cotyledon discs, 6 per sample, were used for gDNA extraction. The gDNA was quantified with the Pico Green™ method according to vendor's instructions (Molecular Probes, Eugene, Oreg.). Samples were diluted by a ⅕ dilution with DNase-free water.

Example 1.2

TaqMan® Assay and Results

Specific TaqMan® primers and probes were designed for cotton event pDAB4468.19.10.3 specific TaqMan® assay. These reagents were used with the conditions listed below to detect the transgene insert within cotton event pDAB4468.19.10.3. Table 1 lists the primer and probe sequences that were developed specifically for the detection of cotton event pDAB4468.19.10.3.

TABLE 1

PCR Primers and Probes

| Name | Description | 5' to 3' sequence |
|---|---|---|
| Event Target Reaction | | |
| (SEQ ID NO: 5) ES_1910_5F | Event specific forward Primer | GGCCTAACTTTTGGTGTGATG |
| (SEQ ID NO: 6) ES_1910_5R | Event specific reverse Primer | AGGTGATTTCGATGATGATATATGTG |
| (SEQ ID NO: 7) ES_1910_5_Pr | Event specific probe used with 5 and 6 | VIC-TGCTGACTGGAAATATACTTATGTA-MGB |
| (SEQ ID NO: 8) ES_1910_3F | Event specific forward Primer | CATTAAAAACGTCCGCAATGTG |
| (SEQ ID NO: 9) ES_1910_3R | Event specific reverse Primer | TGTTGGGTAAGACGGTTCCA |
| (SEQ ID NO: 10) ES_1910_3_Pr | Event specific probe used with 8 and 9 | VIC-AAGCGTCAAAGAAAAG-MGB |
| Reference System Reaction | | |
| (SEQ ID NO: 11) IC_Sah7F | Forward Primer | AGTTTGTAGGTTTTGATGTTACATTGAG |
| (SEQ ID NO: 12) IC_Sah7R | Reverse Primer | GCATCTTTGAACCGCCTACTG |
| (SEQ ID NO: 13) IC_Sah7_Pr | Probe | Cy5-AAACATAAAATAATGGGAACAACCATGACATGT-BHQ2 |

The multiplex PCR conditions for amplification are as follows: 1× Roche PCR Buffer, 0.4 μM event specific forward primer, 0.4 μM event specific reverse primer, 0.4 μM Primer IC_Sah7F, 0.4 μM Primer IC_Sah7R, 0.2 μM Event specific probe, 0.2 μM IC_Sah7Pr Probe, 0.1% PVP, 2 μL of 1:5 diluted gDNA in a total reaction of 10 μl. The cocktail was amplified using the following conditions: i) 95° C. for 10 min., ii) 95° C. for 10 sec, iii) 55° C. for 30 sec, iv) repeat step ii-iii for 40 cycles, v) 40° C. hold. The Real time PCR was carried out on the Roche LightCycler® 480. Data analysis was based on measurement of the crossing point (Cp value) determined by LightCycler 480 software, which is the PCR cycle number when the rate of change in fluorescence reaches its maximum.

The TaqMan® detection method for cotton event pDAB4468.19.10.3 was tested against a different cotton event which contains the aad12 and pat PTUs and non-transgenic cotton variety in duplex format with cotton specific endogenous reference gene, IC Sah7 (GenBank: AY117065.1). The assays specifically detected the cotton event pDAB4468.19.10.3 and did not produce or amplify any false-positive results from the controls (i.e., the different cotton event and non-transgenic cotton variety Coker 310). The event specific primers and probes can be used for the detection of the cotton event pDAB4468.19.10.3 and these conditions and reagents are applicable for zygosity assays.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. A method of detecting cotton event pDAB4468.19.10.3 in a sample comprising cotton DNA, the method comprising:
   contacting the sample with a first primer at least 10 bp in length that selectively binds to a flanking sequence within by 1-1354 of SEQ ID NO:1 or the complement thereof, and a second primer at least 10 bp in length that selectively binds to an insert sequence within by 1355-1672 of SEQ ID NO:1 or the complement thereof; and
   assaying for an amplicon generated between the primers.

2. The method according to claim 1, wherein the sample is from at least one cotton plant comprising event pDAB4468.19.10.3, a representative sample of which has been deposited under ATCC accession number PTA-12457.

3. The method according to claim 1, the method further comprising:
   contacting said sample with a third primer at least 10 bp in length that selectively binds to an insert sequence within by 1-168 of SEQ ID NO:2 or the complement thereof, and a fourth primer at least 10 bp in length that selectively binds to flanking sequence within by 169-2898 of SEQ ID NO:2 or the complement thereof; and
   assaying for an amplicon generated between the primers.

4. The method according to claim 3, wherein the sample is from at least one cotton plant comprising event pDAB4468.19.10.3, a representative sample of which has been deposited under ATCC accession number PTA-12457.

5. The method according to claim 1, wherein the first and second primers are selected from the group of SEQ ID NOs: 5-7.

* * * * *